(12) United States Patent
Yang et al.

(10) Patent No.: US 7,960,589 B2
(45) Date of Patent: Jun. 14, 2011

(54) SYNTHESIS OF SPHINGOSINES AND THEIR DERIVATIVES

(75) Inventors: Hao Yang, Waukegan, IL (US); Lanny S. Liebeskind, Atlanta, GA (US)

(73) Assignee: Emory University, Atlanta, GA (US)

( * ) Notice: Subject to any disclaimer, the term of this patent is extended or adjusted under 35 U.S.C. 154(b) by 113 days.

(21) Appl. No.: 12/440,285

(22) PCT Filed: Sep. 5, 2007

(86) PCT No.: PCT/US2007/077583
§ 371 (c)(1),
(2), (4) Date: Mar. 6, 2009

(87) PCT Pub. No.: WO2008/030840
PCT Pub. Date: Mar. 13, 2008

(65) Prior Publication Data
US 2010/0197954 A1  Aug. 5, 2010

Related U.S. Application Data

(60) Provisional application No. 60/842,624, filed on Sep. 6, 2006.

(51) Int. Cl.
C07C 209/68 (2006.01)
C07C 215/24 (2006.01)
C07C 221/00 (2006.01)
C07C 225/14 (2006.01)

(52) U.S. Cl. ......... 564/468; 564/502; 564/506; 564/509

(58) Field of Classification Search .................. None
See application file for complete search history.

(56) References Cited

U.S. PATENT DOCUMENTS

| | | | | |
|---|---|---|---|---|
| 5,012,000 A | * | 4/1991 | Illig et al. ............... | 564/489 |
| 5,232,837 A | | 8/1993 | Merrill et al. | |
| 5,426,228 A | * | 6/1995 | Koskinen et al. ......... | 564/360 |
| 5,488,166 A | * | 1/1996 | Hudlicky ............... | 564/487 |
| 5,488,167 A | * | 1/1996 | Hudlicky ............... | 564/489 |
| 5,518,879 A | | 5/1996 | Merrill, Jr. et al. | |
| 5,587,494 A | * | 12/1996 | Panzica et al. ............ | 549/512 |
| 6,127,578 A | | 10/2000 | Merrill, Jr. et al. | |
| 6,610,835 B1 | | 8/2003 | Liotta et al. | |
| 6,852,892 B2 | * | 2/2005 | Van Boom et al. ......... | 564/503 |
| 7,138,547 B2 | | 11/2006 | Acena et al. | |
| 7,445,931 B2 | | 11/2008 | Condie et al. | |

OTHER PUBLICATIONS

Garner et. al., Journal of Organic Chemistry (1987), 52, p. 2361-2364.*
Bennacer, et al., A New Route for Total Synthesis of 6,7-Dihydroeponemyin, Eur. J. Org. Chem. 2003, 4569-4574.
Crisp, et al, Palladium-Catalyzed Coupling of L-Proline Acid Chloride with Vinylstannanes, Synth. Commun. 1990, 20 (11) 1665-1670.
Dondoni, et al., Synthesis of 1.1-Dimethylethyl (S)-4-Formyl-2,2-Dimethyl-3-Oxazolidinecarboxylate by Oxidation of the Alcohol, Org. Synth. 2000, 77, 64-77.
Li, et al, Synthesis of High Enantiopurity N-Protected α-Amino Ketones by Thiol Ester-Organostannane Cross-Coupling Using pH-Neutral Conditions, Org. Lett. 2008, 10(19): 4375-4378.
Lu, et al., Total Synthesis of Two Photoactivaable Analogues of the Growth-Factor-Like-Mediator Sphingosine 1-Phosphate: Differential Interaction with Protein Targets, Org. Chem. 2003, 68, 7046-7050.
Merino, et al., Enantiodivergent Synthesis of D- and L-erythro-Sphingosines through Mannich-Type Reactions of N-Benzyl-2-3-O-isopropylidene-D-glyceraldehyde Nitrone, Org. Chem. 2006, 71, 4685-4688.
Milstein, et al., Targeting sphingosine-1-phosphate: A novel avenue for Cancer Therapeutics, Cancer Cell 2006, 9, 148-150.
Rai, et al, Sphingolipid Synthesis via Olefin Cross Metathesis: Preparation of a Differentially Protected Building Block and Application to the Synthesis of D-erythro-Ceramide, Org. Lett. 2004, 6 (17); pp. 2861-2863.
Yang, et al., A Concise and Scalable Synthesis of High Enantiopurity (1)-D-erythro-Sphingosine Using Peptidyl Thiol Ester-Boronic Acid Cross-Coupling, Org. Lett., 2007, 9 (16): 2993-2995.

* cited by examiner

*Primary Examiner* — Brian J Davis
(74) *Attorney, Agent, or Firm* — James C. Mason; Susanne Hollinger; Thomas Kayden Horstemeyer & Risley LLP

(57) ABSTRACT

Embodiments of the present disclosure provide for methods of making sphingosines and derivatives thereof, and the like.

8 Claims, No Drawings

SYNTHESIS OF SPHINGOSINES AND THEIR DERIVATIVES

CROSS REFERENCE TO RELATED APPLICATION

This application claims priority to the PCT application entitled "Synthesis of Sphingosines and Their Derivatives," having serial number PCT/US2007/77583, filed on September, 2007. This application also claims priority to and benefit of U.S. Provisional Patent entitled "Synthesis of Sphingosines and Their Derivatives" having application no. 60/842,624, filed on Sep. 6, 2006, which is incorporated by reference in its entirety.

STATEMENT ON FUNDING PROVIDED BY THE U.S. GOVERNMENT

This invention was made with government support under GM066153 awarded by the National Institutes of Health. The government has certain rights in the invention.

BACKGROUND

Sphingolipids are a major component of cell membranes that play an important role in multiple biochemical processes such as cell growth, programmed cell apoptosis, stress responses, calcium homeostasis, cell migration, angiogenesis and vascular maturation. Sphingolipids are isolated from bio-organisms with a variety of specifically targeted bioactivities. For example, acetylaplidiasphingosines which were isolated from tunicates showed antibacteria and antifungal activity (Carter, J. Am. Chem. Soc. 1978, Vol. 100 (23); pp 7441-7442, which is incorporated herein by reference). In 1997, plakosides were shown to have strong immunosuppressive activity without significant cytotoxicity (Constantino, J. Am. Chem. Soc. 1978, Vol. 119 (51); pp 12465-12470, which is incorporated herein by reference).

Most natural sphingolipids are developed from D-erythro-sphingosine as the core unit. Phosphorylation yields sphingosine phosphates. These phosphorylated sphingolipids regulate a number of cellular processes with stimulatory activity including cell growth, differentiation, angiogenesis and maturation. Acylation of the amino group of the sphingosine produces ceramides, which are an important ingredients in cosmetic products for skin and hair care. Glycosylation of sphingosine results in glycosphingolipids, which have been found to have anticancer and antitumor activities.

Natural sphingolipids are isolated in trace quantities and in a heterogeneous form. Therefore, the synthesis of chemically homogenous sphingosines in high yield and enantiomeric purity is very important for drug discovery and for the cosmetics industry.

A number of synthetic strategies have been developed for producing sphingolipids, especially from sphingosine. However, these synthetic routes can still be economically impractical because of the reaction scale, poor stereoselectivity and E/Z selectivity.

From the methods reported in the literature, the most practical approach for the synthesis of sphingosine and its derivatives begins with the common amino acid, L-serine, as the starting material. It is very logical to start with naturally abundant L-serine because it bears the C-2 S-configuration and C-1 hydroxyl functionality. Garner et al developed a short method for sphingosine synthesis by producing enantiopure serine aldehyde. However, Garner's method did not allow the synthesis of high enantipurity sphingosine (i.e., ee>99%), since 1-3% epimerization occurs in the synthesis serine aldehyde (Garner, J. Org. Chem. 1987, Vol. 52 (12), pp 2361-2364, which is incorporated herein by reference). Therefore, there still exists a need for an economical, scalable, and efficient synthesis of sphingosines.

SUMMARY

Embodiments of the present disclosure provide for methods of making sphingosines and derivatives thereof, and the like.

One exemplary method of making sphingosines and derivatives thereof, among others, includes:

converting a serine acid of formula I to a corresponding thiol ester having formula II, formula I:

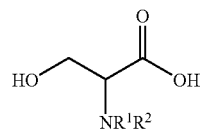

wherein $R^1$ and $R^2$ are each a carbonyl protection group selected from: an acetyl group, an alkyl group, an alkyl acetyl group, a t-butoxycarbonyl (Boc) group, a benzyloxycarbonyl (Cbz) group, and a 9-fluorenylmethoxycarbonyl (Fmoc) group, formula II:

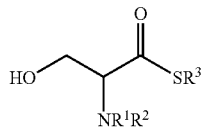

wherein $R^3$ is selected from H, an alkyl group, an aromatic group, and a heteroaromatic ring, optionally each of the aromatic group and the heteroaromatic ring have a substituent X disposed on each carbon of the ring, wherein each X is independently selected from N-isopropyl-benzamide, N-tert-butyl-benzamide, ortho-nitro and combinations thereof;

protecting the serine thiol ester on the 1-OH to give a compound of formula III by reacting the compound of formula II with a silylating agent in the presence of a bulky amine:

formula III:

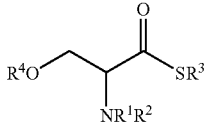

wherein $R^4$ is selected from a silyl group, an ester group, an acetal group, a carbonate group, a glycoyl group, a phosphoryl group, and an ether group, forming a carbon-carbon bond using Liebeskind-Srogl cross-coupling reaction by reacting a thiol ester of formula III with a compound to form a product of formula V, wherein the compound is selected from: alkyl boronic acids, alkenyl boronic acids, alknyl boronic acids, aromatic boronic acids, heteroaromatic boronic acids, alkyl stannanes, alkenyl stannanes, alknyl stannanes, aromatic stannanes, and heteroaromatic stannanes, formula V:

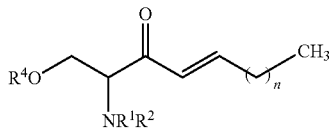

wherein $R^4$ is selected from H, a silyl group, an ester group, an acetal group, a carbonate group, a glycoyl group, a phosphoryl group, and an ether group, wherein n is about 1 to 50, reducing the compound of formula V to form the compound of formula VI, formula VI:

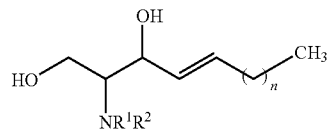

crystallizing the compound of formula VI to produce a compound of formula VII, formula VII:

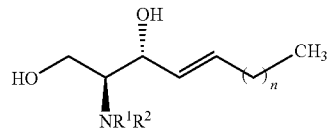

wherein n is about 1 to 50.

DETAILED DESCRIPTION

Embodiments of the present disclosure employ, unless otherwise indicated, techniques of organic chemistry, biochemistry, and the like, which are within the skill of the art. Such techniques are explained fully in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports.

Definitions

In this specification and in the claims that follow, reference will be made to a number of terms that shall be defined to have the following meanings unless a contrary intention is apparent.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In particular, "alkyl" refers to straight or branched chain hydrocarbon groups having 1 to 12 carbon atoms, preferably 1 to 8 carbon atoms, such as methyl, ethyl, n-propyl, i-propyl, n-butyl, i-butyl, t-butyl, pentyl, hexyl, heptyl, octyl, and the like. Lower alkyl groups, that is, alkyl groups of 1 to 6 carbon atoms, are generally most preferred. The term "substituted alkyl" refers to alkyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The term "aliphatic" refers to groups having carbon atoms bonded together in straight or branched chains or in rings, that can be either saturated or unsaturated, but not aromatic.

The term "alkoxy" means an alkyl group linked to oxygen thus: R—O—. In this function, R represents the alkyl group. An example would be the methoxy group $CH_3O$—.

The term "alkenyl" refers to straight or branched chain hydrocarbon groups having 2 to 12 carbon atoms, preferably 2 to 4 carbon atoms, and at least one double carbon to carbon bond (either cis or trans), such as ethenyl. The term "substituted alkenyl" refers to alkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The term "alkynyl" refers to straight or branched chain hydrocarbon groups having 2 to 12 carbon atoms, preferably 2 to 4 carbon atoms, and at least one triple carbon to carbon bond, such as ethynyl. The term "substituted alkynyl" refers to alkynyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "ar" or "aryl" refer to "aromatic" homocyclic (i.e., hydrocarbon) mono-, bi- or tricyclic ring-containing groups preferably having 6 to 12 members such as phenyl, naphthyl and biphenyl. Phenyl is a preferred aryl group. Aromaticity is a chemical property in which a conjugated ring of unsaturated bonds, lone pairs, or empty orbitals exhibit a stabilization stronger than would be expected by the stabilization of conjugation alone. It can also be considered a manifestation of cyclic delocalization and of resonance.

The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and the like, where optionally one or more pair of substituents together with the atoms to which they are bonded form a 3 to 7 member ring.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "carbocyclo", "carbocyclic" or "carbocyclic group" refer to both cycloalkyl and cycloalkenyl groups. The terms "substituted carbocyclo", "substituted carbocyclic" or "substituted carbocyclic group" refer to carbocyclo or carbocyclic groups substituted with one or more groups as described in the definition of cycloalkyl and cycloalkenyl.

The terms "halogen" and "halo" refer to fluorine, chlorine, bromine, and iodine.

The terms "heterocycle", "heterocyclic", "heterocyclic group" or "heterocyclo" refer to fully saturated or partially or completely unsaturated, including aromatic ("heteroaryl") or nonaromatic cyclic groups (for example, 3 to 13 member monocyclic, 7 to 17 member bicyclic, or 10 to 20 member tricyclic ring systems, preferably containing a total of 3 to 10 ring atoms) that have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1-dioxothienyl, and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranly, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo[3.2.1]octane), azaspixoalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl), and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclo" refer to heterocycle, heterocyclic and heterocyclo groups substituted with one or more groups preferably selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, etc., where optionally one or more pair of substituents together with the atoms to which they are bonded form a 3 to 7 member ring.

The term "alkanoyl" refers to alkyl group (which may be optionally substituted as described above) linked to a carbonyl group (e.g., —C(O)-alkyl). Similarly, the term "aroyl" refers to an aryl group (which may be optionally substituted as described above) linked to a carbonyl group (e.g., —C(O)-aryl).

The boronic acid group can include, but is not limited to, arylboronic acids such as phenylboronic acids, naphthalenylboronic acids, quinolinylboronic acids, pyridinylboronic acids, furanylboronic acids, thiophenylboronic acids, indolylboronic acids, 1,8-naphthalimide-based boronic acids, and α-acetaminoalkylboronic acids.

The term "organostanne" refers to tin chemicals bearing a hydrocarbon substituent, such as, but not limited to, $R^1$—$SnR_3$, where $R^1$ is an alkyl, alkenyl, or aryl groups. R is an alkyl group.

The term "yield" refers to the isolated product yield calculated based on molar conversation of one of the starting material.

The term "ee" means the enantiomer excess. The term "de" means diastereomer excess. Their values (%) are measured by HPLC analyses using enantiomer or diastereomer mixtures.

Discussion

Embodiments of the disclosure provide for a synthesis of sphingosines and their derivatives. In particular, embodiments of the disclosure provide for a mild and efficient synthesis of sphingosines and their derivatives, where all the reactions are conducted at or near room temperature and under non-basic conditions (not greater than a pH of about 7). In an embodiment, the synthesis of D-erythro-sphingosine provides a high overall yield (e.g., about 40-60% in 4 steps or about 60-75% in 6 steps) in high enantiomeric purity (e.g., up to 87-99% de and 97-99% ee) can be achieved using embodiments of this disclosure. In embodiments of this method of synthesis, commercially available and inexpensive N-protected-serine was selected as the starting material. In general, the total process includes, but is not limited to, thio esterification, 1-OH protection, cross-coupling, deprotection, asymmetric reduction, and deprotection. This process can be scaled up to a multi-kilogram level. Using this process, various ceramides can be made by acylating at the 2-amino group using acid or acid chloride.

Of these, those using the inexpensive amino acid serine as the starting material are the most economical since L-serine bears C-1 hydroxyl group and the C-2 chiral center of sphingosine. However, reported synthetic methods using serine can sometimes be complicated by the ease with which the α stereocenter of derivatives of the amino acid is racemized under both acidic and basic condition. Embodiments of the present disclosure utilize extremely mild thioesters and boronic acids/organostananes cross coupling to make the ketone precursor without racemization.

As mentioned above, embodiments of this disclosure include a mild, short, and scalable process to synthesize sphingosines (4 or 6 linear steps) and ceramide (5 or 7 linear steps) in both high overall yield (about 40-75%) and enantiomeric purity (about 88-99% de and about 97-99% ee) starting with commercially available serine. Only a few steps are needed to achieve simple chromatographic purification, and thus, embodiments of this procedure can be used on an industrial scale to manufacture sphingosines in bulk.

An embodiment of a method for making sphingosines and ceramide is described below. Initially, an N-protected serine was employed as the starting material, representatively as formula I.

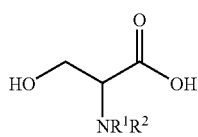

(formula I)

$R^1$ and $R^2$ each can include a carbonyl protection group such as, but not limited to, Ac (acetyl), AlkylAc(alkyl acetyl), Boc (t-butoxycarbonyl), Cbz (benzyloxycarbonyl), and Fmoc (9-fluorenylmethoxycarbonyl). The 2-amino group may be mono-protected or di-protected.

The first step is to convert the serine acid (formula I) to the corresponding thiol ester (formula II).

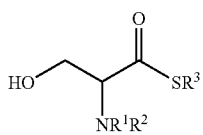

(formula II)

$R^3$ can be H, an aliphatic group, an aromatic or heteroaromatic ring, which may have a substituent X on the ortho, meta, and para positions. In another embodiment, the substituent X can be located at any position about the aromatic or heteroaromatic ring. X can be derived from any atom except metal (e.g., C, O, S, N, halogen, and the like). In particular, X or each X, if more than one, can be independently selected from one or more of the following: N-isopropyl-benzamide, N-tert-butyl-benzamide, ortho-nitro and combinations thereof.

A typical peptide condensation reaction is chosen to perform this conversion, including several operations to give the thioester in a yield of about 47-89% mol %.

1. The solvent for this step is a polar non-protic solvent that is dried before using. For example, the solvent can include, but is not limited to ethyl acetate, methylene dichloride, acetonitrile, or DMF.
2. A racemization inhibitor, excessive thiol ($R^3SH$), or similar compound may be present during the reaction process between serine acid (formula I), thiol ($R^3SH$) and condensation reagent.

The final thioester synthesized was determined to have enantiopurity (>about 97-99% ee and about 88-99% de) by HPLC analysis.

The second step is to protect the serine thiol ester on the 1-OH to give the compound III (formula III).

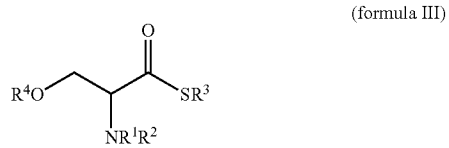

(formula III)

$R^4$ can include protecting groups such as, but not limited to, silyl groups (e.g., TMS (trimethylsilyl) and TBS (t-butyldimethylsilyl)); ester groups (e.g., Ac (acetyl) and Bz (benzoyl)); acetal groups (e.g., THP (tetrahydropyranyl), and MEM (methoxymethyl)); carbonate groups (e.g., benzyl carbonate and p-nitrobenzyl carbonate); glycoyl groups (HO—R—OH, e.g. glucosyl, pyranosyl or galatosyl)); phosphoryl groups (—P=O) or ether groups (e.g., Bn (benzyl) and Tr (trityl)).

Embodiments using a silyl group as the protecting group, thiol ester II (formula II) is reacted with a silylating agent in the presence of a bulky amine as the base. The silylating agent can include, but is not limited to, a trialkylsilyl chloride and a trialkylsilyl triflate. The addition of a catalyst (e.g., catalytic DMAP) can promote the reaction process. This protecting step results in a quantitative yield.

(formula IV)

$MX_n$=B(OH)$_2$, or SnR$_3$ (R=an alkyl)
n=0-50, 10-20, or 12 for sphingosine

In other embodiments, the compound of formula IV can be replaced with a compound such as, but not limited to, alkyl boronic acids, alkenyl boronic acids, alknyl boronic acids, aromatic boronic acids, heteroaromatic boronic acids, alkyl stannanes, alkenyl stannanes, alknyl stannanes, aromatic stannanes, and heteroaromatic stannanes.

The third step is a ketone synthesis to form the carbon-carbon bond using Liebeskind-Srogl cross coupling reaction conditions. This cross coupling is conducted at room temperature with dried THF as the solvent under an argon or nitrogen atmosphere. About 10-40 mol % of a phosphite or a phosphine ligand is employed to eliminate the possible decarbonylation side reaction and give a yield from about 80 to 94%. An alkyl vinyl (cis or trans) alkenylboronic acid or alkenylstannane IV (formula IV)(having 3-50 carbon atoms)

is used as the coupling partner. The thioester III (formula III) coupling with the alkenylboronic acid or alkenylstannane IV (formula IV) gives a clean colorless oil like product without any epimerization at the chiral center on the α position of the resulting ketone product V.

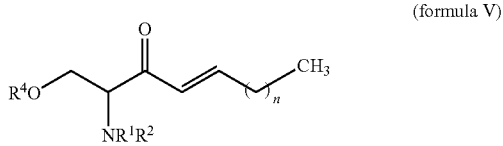
(formula V)

$R^4$ can include protecting groups such as, but not limited to, H, silyl groups (e.g., TMS (trimethylsilyl) and TBS (t-butyldimethylsilyl)); ester groups (e.g., Ac (acetyl) and Bz (benzoyl)); acetal groups (e.g., THP (tetrahydropyranyl) and MEM (methoxymethyl)); carbonate groups (e.g., benzyl carbonate and p-nitrobenzyl carbonate); glycoyl groups; phosphoryl groups or ether groups (e.g., Bn (benzyl) and Tr (trityl)).

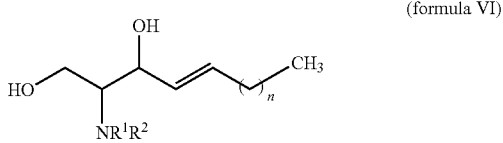
(formula VI)

The fourth step is the reduction of the ketone V (formula V) using a suitable reducing reagent (e.g., $NaBH_4$, $LiAl(O\text{-}tert\text{-}Bu)_3$, and $Zn(BH_4)_2$). Based on the substrate V (formula V), a satisfactory diastereomeric selectivity (e.g., about 5:1 to 31:1) was achieved. For example, using a $LiAl(O\text{-}tert\text{-}Bu)_3$ reaction system generates the desired stereo isomer with about 31:1 selectivity. Afterwards, the use of an easy crystallization procedure produces the diol VI (formula VI) with high diastereopurity (>about 97-99% de).

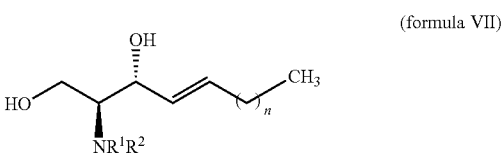
(formula VII)

Deprotection of VII (formula VII) is generally accomplished quantitatively using, but is not limited to, TFA (trifluoroacetic acid), and/or HCl (hydrogen chloride), to give the resulting sphingosine VIII (formula VIII) when n is 1 to 50, 10 to 20, and 12.

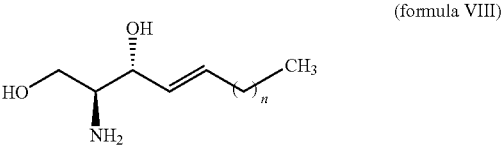
(formula VIII)

Sphingosine VIII (formula VIII) is converted to Ceramide IX (formula IX) by reaction with acid chloride Y ($C_nH_{2n-1}COCl$, n=1-50) or acid X ($C_nH_{2n-1}COOH$, n=1-50) in the presence of suitable condensation reagent such as dicyclohexylcarbodiimide, EDI, BOP.

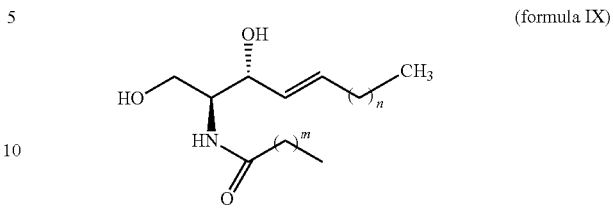
(formula IX)

m=0-50

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified. In addition, the phrase "about 'x' to 'y'" includes "about 'x' to about 'y'".

The above discussion is meant to be illustrative of the principles and various embodiments of the present disclosure. Numerous variations and modifications will become apparent to those skilled in the art once the above disclosure is fully appreciated. It is intended that the following claims be interpreted to embrace all such variations and modifications.

EXAMPLE

Now having described the embodiments of the disclosure, in general, the example describes some additional embodiments. While embodiments of present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

Example

For example, ($R^1$=Cbz, Boc, or Fmoc, $R^2$=H) protected serine with L or D configuration are widely commercially available from Sigma-Aldrich, Acros and other major chemical companies.

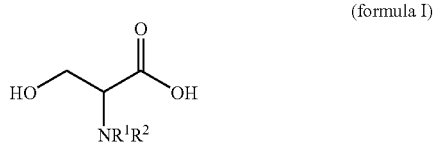
(formula I)

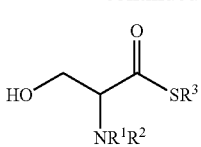
(formula II)

($R^1$ = H, $R^2$ = Cbz, $R^3$ = phenyl)

Procedure: Thiophenol (about 1-20 equiv.) was added to a THF solution of N-Cbz-L-Serine (about 10 mmol (1 equiv), about 4 ml/mmol) at about 0-30° C., followed by HOBT (1 equiv) and 1,3-dicyclohexylcarbodiimide (1.1 equiv). The mixture was stirred for about 3-24 hours at room temperature and the reaction progress was monitored by TLC analysis. After completion of the reaction, a few drops of acetic acid were added to remove the excess 1,3-dicyclohexylcarbodiimide. About thirty minutes later, the reaction solution was filtered to remove the dicyclohexylurea and washed sequentially with about 0.1 M HCl, followed with saturated NaHCO$_3$ and then brine solution. The combined organic layer was concentrated under vacuum and the residue was crystallized in ethyl acetate and hexane (1:1) to generate the thiophenyl ester (formula II) in about 75-94% yield (about 2.94 gram), Mp=108-110° C. TLC($R_f$=0.40, silica gel, ethyl acetate/hexanes=1:1). ee about 85-99% was determined by HPLC analysis using the corresponding racemic mixture for comparison. $^1$H NMR (400 MHz, CDCl$_3$) δ 7.43-7.31 (m, 10H), 5.87 (d, J=8.8 Hz, 1H), 5.20 (s, 2H), 4.64 (m, 1H), 4.17 (dd, J=11.2, 2.8 Hz, 1H), 3.86 (dd, J=11.6, 4.0 Hz, 1H). $^{13}$C NMR (100 MHz, CDCl$_3$) δ 198.9, 156.3, 136.1, 134.8, 129.9, 129.5, 128.8, 128.5, 128.4, 126.9, 67.7, 63.2, 62.4. IR (neat, cm$^{-1}$) 3377 (br), 3065 (w), 2937 (w), 1698 (s), 1521 (s), 1254 (s), 1058 (s), 694 (m). HRMS (FAB) Calcd for C$_{17}$H$_{18}$NO$_4$S ([M+H]$^+$): 332.0951. Found: 332.0944.

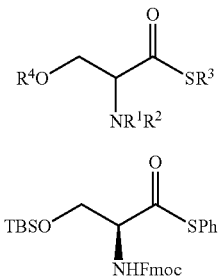
(formula III)

(formula IIIb)

For example:

Procedure for formula Mb: A mixture of thiophenyl ester formula IIb (formula II where $R^1$=H, $R^2$=Fmoc, $R^3$=Ph) (about 2-40 mmol), tert-butyldimethylsilane chloride (about 1.2-10.0 equiv.) and 4-dimethylaminopyridine (about 10-40 mol %) in dry dichloromethane (about 5-30 ml/mmol) was added to N-methylmorpholine (about 1.0-5.0 equiv.) followed by stirring at about room temperature for about 3-24 hours. The reaction crude was washed sequentially with ammonium chloride aqueous solution, saturated aqueous NaHCO$_3$ and brine. The organic layer was concentrated under vacuum to afford the thiolester nab in quantitative yield. TLC($R_f$=0.5, silica gel, ethyl acetate/hexane=1:4). ee>about 98-99%. $^1$H NMR (400 MHz, CDCl$_3$) δ 7.78 (d, J=7.6 Hz, 2H), 7.67 (t, J=8.4 Hz, 2H), 7.43-7.37 (m, 7H), 7.33 (t, J=7.2 Hz, 2H), 5.80 (d, J=8.8 Hz, 1H), 4.57 (m, 2H), 4.40 (t, J=8.0 Hz, 1H), 4.34 (t, J=7.2 Hz, 1H), 4.21 (dd, J=10.0, 2.4 Hz, 1H), 3.83 (dd, J=3.6, 10.0 Hz, 1H), 0.94 (s, 9H), 0.09 (d, J=5.2 Hz, 6H).
$^{13}$C NMR (100 MHz, CDCl$_3$) δ 198.8, 156.1, 144.0, 143.8, 141.5, 134.8, 129.7, 129.4, 128.0, 127.5, 127.3, 125.4, 125.3, 120.3, 67.7, 63.7, 62.4, 47.4, 26.0, 18.5, −5.3. IR (neat, cm$^{-1}$) 2953 (m), 1702 (s), 1498 (m), 1252 (m), 1108 (s), 837 (m), 706 (m). HRMS (FAB) Calcd for C$_{30}$H$_{36}$NO$_4$SSi ([M+H]$^+$): 534.2128. Found: 534.2124.

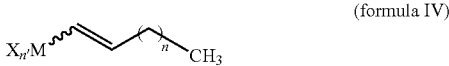
(formula IV)

Alkenylboronic acids and alkenylstannanes (formula IV) are commercially available. For those unavailable for purchase, their syntheses are well described in the literature, typically by hydroboration or hydrostannylation of a terminal acetylene followed by hydrolysis. (Brown, *Organometallics* 1983, Vol. 2 (10), 1311-1316, which is incorporated herein by reference)

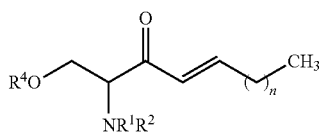
(formula V)

For example,

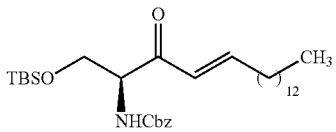
(formula Vg)

Procedure:

A mixture of thiol ester formula IIIg (formula III, where $R^1$=H, $R^2$=Cbz, $R^3$=Ph, $R^4$=TBS) (about 1.0-10 mmol, about 0.679-6.794 g), boronic acid formula IV$_{15}$ (about 1.0-2.0 equiv.), Cu(I) thiophene carboxylate (about 1.0-2.0 equiv.) and Pd$_2$(dba)$_3$ (about 0.5-2.5 mol %) was placed under an argon atmosphere. THF (about 10-200 mL) and triethylphosphite (about 20 mol %) were added and the mixture was stirred at about room temperature for about 3-16 hours. For work up, the reaction mixture was diluted with about 50-400 mL ethyl acetate, washed with saturated NaHCO$_3$ aqueous solution and brine, following by drying over MgSO$_4$. After filtration and concentration under vacuum, the reaction crude was purified by chromatography on silica gel using about 20:3 EtOAc:hexane to give about 0.8-6.5 g (about 85-94%) pure ketone (formula Vg). TLC($R_f$=0.6, silica gel, hexane/ethyl acetate=5:1). ee=about 97-99%, absolute 4,5-E-alkene product; the Z-product was not observed from NMR. $^1$H NMR (400 MHz, CDCl$_3$) δ 7.36-7.28 (m, 5H), 6.98 (dt, J=15.6, 6.8 Hz, 1H), 6.28 (d, J=15.6 Hz, 1H), 5.82 (d, J=7.6 Hz, 1H), 5.11 (s, 2H), 4.60 (m, 1H), 4.00 (dd, J=3.2, 10.0 Hz, 1H), 3.85 (dd, J=4.8, 10.4 Hz, 1H), 2.22 (q, J=7.2, 14.0 Hz, 2H), 1.45 (m, 2H), 1.26 (m, 20H), 0.88 (t, J=6.8 Hz, 3H), 0.83 (s, 9H), −0.01 (s, 6H). $^{13}$C NMR (100 MHz, CDCl$_3$) δ 196.0, 156.0, 149.8, 136.6, 128.7, 128.3, 128.2, 126.8, 67.0, 63.7, 60.1, 32.8, 32.1, 29.8, 29.7, 29.6, 29.5, 29.4, 28.2, 25.9, 22.9, 18.3, 14.3, −5.3, −5.4. IR (neat, cm$^{−1}$) 3428 (w), 2926 (s), 2856 (s), 1725 (s), 1698 (s), 1498 (s), 1112 (s), 837 (m), 689 (m). HRMS (FAB) Calcd for $C_{32}H_{56}NO_4Si$ ([M+H]$^+$): 546.3973. Found: 546.3967.

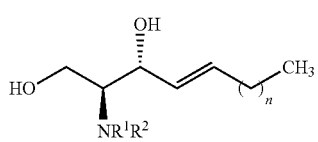

(formula VII)

For example,

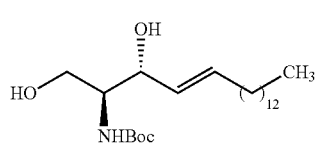

(formula VIIa)

To a solution of ketone Va (about 0.15-1.5 mmol, about 61-610 mg) in anhydrous THF (about 1-10 mL) and dried methanol (about 0.5-5.0 mL) at about −78° C. under argon, was added methoxydiethylborane (1.0-1.5 equiv.) dropwise; the resulting mixture was then stirred for about 10-30 minutes. Subsequently, sodium borohydride (about 1.0-1.2 equiv. about 6.8-68.0 mg) was added. The reaction mixture was stirred for about 6 hours, and about 0.2 mL of acetic acid was added when all ketone starting material was consumed. The reaction mixture was worked up with aqueous sodium bicarbonate solution and concentrated in vacuum. The concentrated organic residue was then azeotroped with about 10-100 mL methanol until all the boronate was decomposed to the corresponding 1,3-diols. Purification of the crude diols was obtained via recrystallization (acetonitrile:hexane=about 2:1) to give about 91% yield of N-Boc-D-erythro-sphingosine VIIa. Mp=63-64° C. TLC(R$_f$=0.3, silica gel, hexane/ ethyl acetate 1:1). ee>about 97-99%, de=about 88-99%. $^1$H NMR (600 MHz CDCl$_3$) δ 5.77 (dt, J=15.6, 7.8 Hz, 1H), 5.26 (dd, J=15.6, 6.6 Hz, 1H), 5.32 (d, J=7.2 Hz, 1H), 4.30 (s, 1H), 3.92 (dd, J=11.4, 3.6 Hz, 1H), 3.69 (dd, J=11.4, 3.0 Hz, 1H), 3.59 (s, 1H), 2.85 (br, 2H), 2.21 (dd, J=14.4, 7.2 Hz, 2H), 1.44 (s, 9H), 1.35 (m, 2H), 1.25 (m, 20H), 0.87 (t, J=6.6 Hz, 3H). $^{13}$C NMR (100 MHz, CDCl$_3$) δ 156.4, 134.4, 129.1, 80.0, 75.2, 62.9, 55.5, 32.5, 32.1, 29.9, 29.8, 29.7, 29.6, 29.4, 29.3, 28.6, 22.9, 14.3. IR (neat, cm$^{−1}$) 3347 (br), 2926 (s), 1718 (m), 1502 (m), 1254 (m), 1173 (m), 837 (m). HRMS (FAB) Calcd for $C_{23}H_{46}NO_4$ ([M+H]$^+$): 400.3421. Found: 400.3420. [α]$^{20}_D$=−1.5 (c=1.12, CHCl$_3$)

For example,

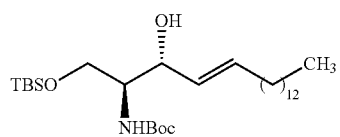

(formula VIIb)

To a solution of ketone Vb (formula V, where R$^1$=H, R$^2$=Boc, R$^3$=TBS) (about 0.1-2.0 mmol, about 50-1000 mg) in anhydrous Ethanol (about 1-10 mL) at about −78° C. under argon, was added LiAl(O-tert-Bu)$_3$ (0.5 M in THF solution) (1.0-1.5 equiv.) dropwise; the resulting mixture was then stirred for about 10-30 minutes at −78° C. The reaction mixture was slowly warmed up to room temperature and stirred for about 2 hours, then the reaction was quenched by 1M HCl. The reaction mixture was worked up with aqueous sodium bicarbonate solution and concentrated in vacuum. The concentrated organic residue was purified by flash chromatography on silica gel (ethyl acetate:hexane=about 1:2) to give about 96% yield of VIIb. TLC(R$_f$=0.60, silica gel, hexane/ ethyl acetate=10:1). ee>about 97-99%, de=about 94-99%. $^1$H NMR (400 MHz, CDCl$_3$) δ 5.75 (dt, J=15.2, 6.8 Hz, 1H), 5.51 (dd, J=15.2, 6.0 Hz, 1H), 5.24 (d, J=8.0 Hz, 1H), 4.19 (t, J=4.8 Hz, 1H), 3.94 (dd, J=10.0, 3.0 Hz, 1H), 3.82 (d, J=7.6 Hz, 1H), 3.56 (m, 1H), 2.05 (app q, J=6.8 Hz, 2H), 1.45 (s, 9H), 1.37 (m, 2H), 1.33 (m, 20H), 0.88 (m, 12H), 0.07 (d, J=1.2 Hz, 6H). $^{13}$C NMR (100 MHz, CDCl$_3$) δ 156.0, 133.3, 129.6, 79.7, 74.9, 63.7, 54.6, 32.5, 32.1, 29.9, 29.7, 29.6, 29.4, 28.6, 26.0, 22.9, 18.3, 14.3, −5.4, −5.4. IR (neat, cm$^{−1}$) 3451 (br), 2926 (s), 1718 (m), 1502 (m), 1254 (m), 1173 (m), 837 (m). HRMS (FAB) Calcd for $C_{29}H_{60}NO_4Si$ ([M+H]$^+$): 514.4286. Found: 514.4282. [α]$^{20}_D$=+11.0 (c=0.91, CHCl$_3$).

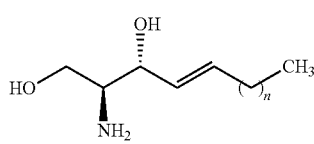

(formula VIII)

For example,

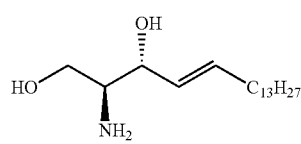

(formula VIII$_{15}$)

To a dichloromethane solution of VIIa (about 1 mmol), was added about 20-70% TFA solution in dichloromethane (about 10 mL) followed by stirring at about 50° C. for about 2 hours. The crude was subsequently quenched by ice water, adding about 1M NaOH aqueous solution till pH=about 10. The solution was then extracted about three times by ethyl acetates. The combined organic layers were concentrated in vacuum. The resulting product was solidified in hexane to generate VIII$_{15}$ as a white powder with a quantitative yield (about 295 mg). TLC(R$_f$=0.3, silica gel, CHCl$_3$/CH$_3$OH/ NH$_4$OH=135:25:4). ee=about 97-99, de=about 88-99%. $^1$H NMR (400 MHz CDCl$_3$) δ 5.73 (dt, J=15.2, 7.4 Hz, 1H), 5.45 (dd, J=15.2, 6.8 Hz, 1H), 4.0 (s, 1H), 4.30 (s, 1H), 3.65 (m, 2H), 2.83 (s, 1H), 2.68 (br s, 4H), 2.04 (q, J=7.2 Hz, 2H), 1.37 (m, 2H), 1.25 (m, 20H), 0.87 (t, J=6.8 Hz, 3H). $^{13}$C NMR (100 MHz, CDCl$_3$) δ 134.8, 129.4, 75.3, 63.9, 56.3, 32.6, 32.1, 29.9, 29.8, 29.7, 29.6, 29.5, 29.4, 22.9, 14.3. IR (neat, cm$^{−1}$) 3366 (br), 2918 (s), 2853 (m), 1467 (m), 1046 (m), 968 (m). HRMS (FAB) Calcd for $C_{18}H_{38}NO_2$ ([M+H]$^+$): 300.2897. Found: 300.2895. [α]$^{20}_D$=−1.4 (c=1.5, CHCl$_3$).

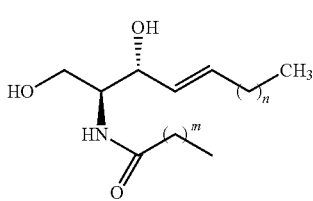

(formula IX)

For example,

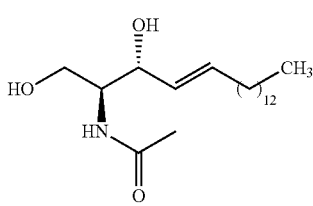

(formula IX$_{15-2}$)

There are several known methods to synthesize compound formula IX$_{15-2}$ from VIII$_{15}$. For example, condensation of VIII$_{15}$ with acetic anhydride was able to afford ceramide IX$_{15-2}$ in about 97% yield. (Mancini, *Helv. Chim. Acta.*, 1994, 51, which is incorporated herein by reference)

What is claimed:

1. A method of making a compound of formula V,

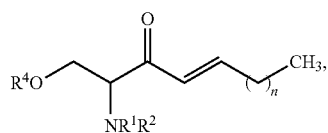

formula V comprising reacting a compound of formula III,

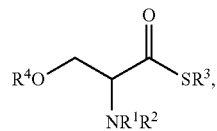

formula III with an compound of formula IV,

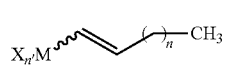

formula IV under conditions such that a compound of formula V is formed, wherein
n is 0 to 50;
$MX_{n'}$ is $B(OH)_2$;
$R^1$ is H or a protecting group comprising a carbonyl group;
$R^2$ is a protecting group comprising a carbonyl group;
$R^3$ is selected from H, an alkyl, substituted alkyl, aryl, substituted aryl, heterocycle, or a substituted heterocycle; and $R^4$ is a protecting group, wherein the protecting group comprises a group selected from the list consisting of a silyl group, an ester group, an acetal group, a carbonate group, a glycoyl group, a phosphoryl group, and an ether group.

2. The method of claim 1, wherein n is 12.
3. The method of claim 1, wherein $R^1$ is H.
4. The method of claim 1, wherein $R^2$ is t-butoxycarbonyl (Boc), a benzyloxycarbonyl (Cbz), or a 9-fluorenylmethoxycarbonyl (Fmoc).
5. The method of claim 1, wherein $R^3$ is a phenyl.
6. The method of claim 1, wherein $R^4$ is a tert-butyldimethylsilyl, triisopropylsilyl, or tert-butyldiphenylsilyl.
7. A method of making a compound of formula V,

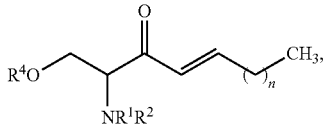

formula V comprising reacting a compound of formula III,

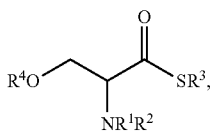

formula III with an alkyenylstannane under conditions such that a compound of formula V is formed, wherein
n is 0 to 50;
$R^1$ is H or a protecting group comprising a carbonyl group;
$R^2$ is a protecting group comprising a carbonyl group;
$R^3$ is selected from H, an alkyl, substituted alkyl, aryl, substituted aryl, heterocycle, or a substituted heterocycle; and
$R^4$ is a protecting group, wherein the protecting group comprises a group selected from the list consisting of a silyl group, an ester group, an acetal group, a carbonate group, a glycoyl group, a phosphoryl group, and an ether group.

8. A method of making a compound of formula VIII,

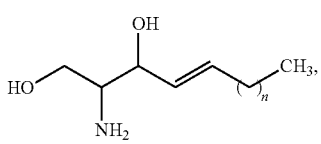

formula VIII comprising,
a) reacting a compound of formula V as in claim 1 with a reducing agent under conditions such that a compound of formula VI is formed,

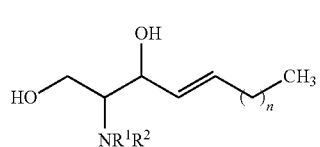
formula VI
and
b) reacting a compound of formula VI with an acid, base, or hydrogen under conditions such that a compound of formula VIII is formed.
* * * * *